United States Patent [19]

Nikiforov et al.

[11] Patent Number: 4,841,982
[45] Date of Patent: Jun. 27, 1989

[54] PLETHYSMOGRAPHIC MEASURING CHAMBER

[75] Inventors: Andrey Nikiforov, Flemington, N.J.; Roger Ventrone, Lucinges/Bonne, France

[73] Assignee: Research & Consulting Company A.G., Itingen, Switzerland

[21] Appl. No.: 136,322

[22] Filed: Dec. 22, 1987

[30] Foreign Application Priority Data

Dec. 22, 1986 [CH] Switzerland ................... 05128/86

[51] Int. Cl.[4] .......................................... A61M 15/00
[52] U.S. Cl. .................................. 128/716; 128/747; 128/200.14; 128/203.12
[58] Field of Search ................. 128/716–730, 128/200.18, 200.14, 203.12, 207.18, 747, 200.22

[56] References Cited

U.S. PATENT DOCUMENTS 4,402,315 9/1983 Tsuda et al. .................... 128/716 X
4,660,572 4/1987 Muruyama et al. ................ 128/804

OTHER PUBLICATIONS

Depledge et al.; "A Technique for Measuring Carbon Monoxide Uptake in Mice"; *Int. I. Radiation Oncology. Biol. Phys.*, vol. 7, No. 4, 4–1981, pp. 485–489.

Primary Examiner—Kyle L. Howell
Assistant Examiner—Angela D. Sykes
Attorney, Agent, or Firm—Cushman, Darby & Cushman

[57] ABSTRACT

The chamber comprises a tubular body terminating in front in a part shaped as a truncated rectangular cone. Two elastomeric rings are for adjusting around the snout of an animal, such as a rat or guinea pig. A piston bounds the space occupied by the animal's body. A collar disposed between the two rings comprises two annular segments each secured to a rod extending radially towards the exterior and secured to an actuating means and associated with a cam. A spring constantly urges the segments towards the interior. The collar is for adjusting behind the animal's head to prevent it from moving back.

4 Claims, 1 Drawing Sheet

PLETHYSMOGRAPHIC MEASURING CHAMBER

BACKGROUND OF THE INVENTION

The invention relates to a plethysmographic measuring chamber for receiving the body of a laboratory animal for measuring various respiratory parameters, of the kind comprising a tubular body having a frustoconical portion at its front end terminating in an aperture for admitting a flow of gas for inhaling, the chamber being bounded at the inlet opening by two axially separated annular seals having respective openings for receiving the animal's snout, whereas the other end of the chamber is bounded by a piston for adjusting the volume of the chamber to the size of the animals.

Chambers of this kind are used for measuring various respiratory parameters of a laboratory animal subjected to tests by inhalation of gas or aerosols formed from various substances. The gas flow resulting from variations in the volume of the animal's body is measured by a transducer and the resulting signal is processed in dependence on the parameters which it is desired to know. This method of measurement and treatment of the detected signal is described in detail in an article "Measurement of respiratory patterns in rodents using whole-body plethysmography and a pneumotachograph" published in Laboratory Animals No. 15 (1981), pages 137-140.

Clearly, the accuracy of measurement cannot be ensured unless the volume of gas in the plethysmographic chamber varies only with variations in volume of the animal's body resulting from the volume of inhaled gas or aerosol. If the gas or aerosol to be inhaled is made up of irritating substances, the animal instinctively tries to escape the flow of gas or aerosol sent to it through the inlet aperture in the tubular body, towards which its snout is directed. These efforts by the animal to pull back are limited by the piston but induce erratic variations in the volume of the plethysmographic chamber, resulting in considerable noise in the signal recorded by the transducer. The noise is difficult to filter and distorts the calculated parameters and consequently interferes with evaluation of the respiratory conditions of the animal subjected to the inhalation test.

The aim of the invention is at least partly to obviate these disadvantages so as to make the measurement more precise and therefore more reliable.

SUMMARY OF THE INVENTION

The present invention provides a plethysmographic measuring chamber for receiving the body of a laboratory animal for measuring respiratory parameters, the chamber having two ends and comprising a tubular body having a front end, and a tapered portion at said front end, the tapered portion terminating in an aperture for admitting a flow of gas to the chamber for inhaling by the animal therein, and adjacent the aperture, two annular seals spaced apart along a longitudinal chamber axis and provided with openings for admitting the snout of an animal placed in the chamber. The seals define one end of the chamber and a movable wall defines the other end, the wall being adjustable in position to adapt the volume of the chamber to the size of the animal therein. A retaining collar is disposed in the spacing between the seals which comprises two mutually opposite members each concave towards the axis of the chamber, mounting means for the concave members such that the members are movable towards and away from one another, and positioning means external of the chamber, adapted to position the concave members at selected radial positions relative to the chamber axis.

The purpose of the collar is to prevent the animal from moving its head back and thus substantially increasing the volume occupied in the plethysmographic chamber when it tries to escape the stream of gas or aerosol distributed through the inlet opening. It is impossible to squeeze the animal with the piston. The piston is adapted only to limit the volume of the plethysmographic chamber to the animal's size but not to squeeze it, in which case the animal could not breathe normally. If the animal is prevented by the collar from moving its head, the volume occupied by its body in the plethysmographic chamber varies only with the volume of inhaled and exhaled air, so that the measurement is characteristic of the animal's respiration and the signal noise is limited to a very low level.

BRIEF DESCRIPTION OF THE DRAWINGS

An embodiment of the plethysmographic measuring chamber according to the invention is shown diagrammatically by way of example in the accompanying drawings in which.

DESCRIPTION OF PREFERRED EMBODIMENTS

Figure 1:
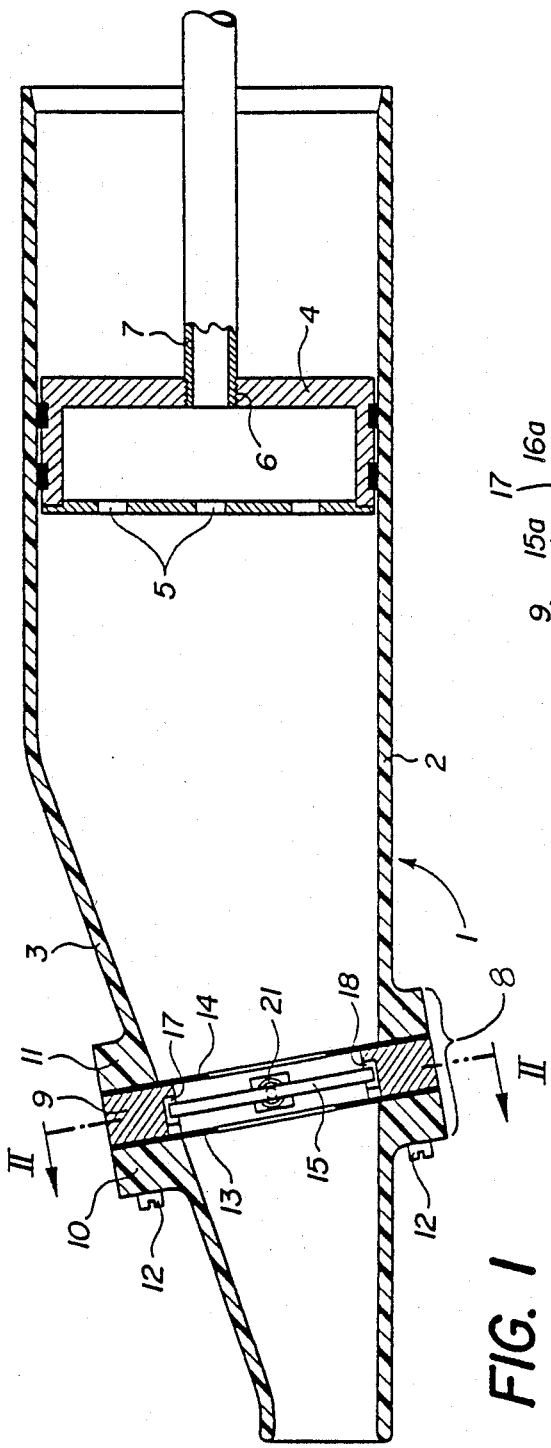
FIG. 1 is a side view in section of the tubular body in which the chamber is formed.

FIG. 1 shows a plethysmographic chamber 1 comprising a cylindrical part 2 and a front part in the form of a truncated rectangular cone 3. The cylindrical part 2 encloses a hollow piston 4, the inner surface of which is formed with openings 5 for communicating with the interior of the tubular body 1 whereas the outer surface of the piston is formed with a threaded opening 6 for screwing the end of a duct 7.

The frustoconical part 3 is divided in two by an annular element 8 comprising a ring 9 held between two annular projections 10, 11 integral with two respective portions of the frusto-conical part 3, which are joined by clamping screws 12. Sheets of an elastomer cut into rings 13, 14 are clamped between the two respective surfaces of ring 8 and the annular projections 9 and 10. The elastomeric rings extend radially inside the space bounded by the frusto-conical part 3. The openings in rings 13, 14 are adapted to admit the snout of the rodent, in the present case a rat or guinea-pig, by being deformed towards the front and thus producing a sealing-tight barrier. The volume bounded by piston 4 on the one hand and rings 13, 14 on the other hand constitutes the plethysmographic chamber.

Figure 2:
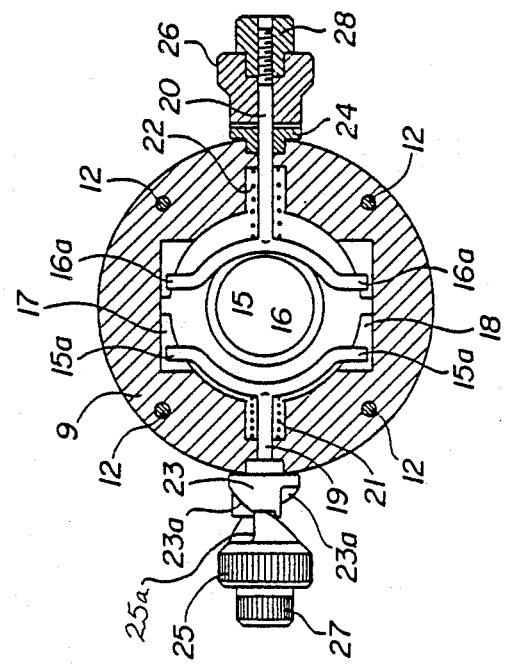
FIG. 2 is a view in section along II—II of FIG. 1.

A retaining collar is disposed in the space between the elastomer rings 13, 14 and bounded by the central ring 9 and is for fitting behind the animal's head. The collar (FIG. 2) comprises two annular segments 15, 16 terminating in two straight segments 15a, 16a facing the exterior. The two straight segments of a single annular segment are situated on a common straight line and extend into two respective recesses 17, 18 diametrically opposite and formed in the central ring 9 and extending in the plane of the opening formed by the collar. Each annular segment 15, 16 is secured at its center to two rods 19, 20 respectively which extend radially towards the exterior and are mounted for sliding through the central ring 9. Two helical springs 21, 22 are wound round rods 19, 20 respectively and are compressed between the annular segments 15, 16 and ring 9, thus constantly urging the annular segments 15, 16 towards one another.

Where they emerge from ring 9, rods 19, 20 extend through two cylindrical studs 23, 24 secured at two diametrically opposite places on ring 9 and each comprising two cams 23a in the form of portions of a helix. The cams on studs 24 are not visible since the stud is shown in section. The two cams for each cylindrical stud are diametrically opposite with respect to the stud axis. Two knurled actuating means 25, 26 are mounted for rotation on respective rods 19, 20. The parts of the actuating means 25, 26 facing the cams on the respective studs 23, 24 have helical cams 25a complementary with cams 23a. The cams on means 26 are not visible since this is shown in section.

Rods 19, 20 end in threaded parts which are screwed into abutment means 27, 28 respectively which, under the action of forces exerted by springs 21 and 22, resiliently press the actuating means 25, 26 against the respective studs 23, 24. By means of this mechanism, therefore, the actuating means 25, 26 can be turned in the suitable direction around the respective rods 19, 20 so as axially to move rods 19, 20 when the helical cam 25a, and a like cam, not shown, on the actuating means 26, slide against the fixed helical cams of studs 23, 24. Consequently, rods 19, 20 can each occupy two radial positions with respect to rod 9, thus likewise controlling two positions of the annular segments 15, 16 corresponding to two spacing between these annular segments. If the difference between the two spacings is fixed and given by the radial length of cam 23a and a like cam, not shown on stud 24, the abutment means 27, 28 can be used for fine adjustment of the respective positions of the annular segments 15, 16 by screwing or unscrewing the ends of rods 19, 20 in the abutment means 27, 28 respectively. The minimum opening of the annular segments can thus be adjusted to the size of the animal. The collar opening should be less than the diameter of its head without squeezing its neck.

Because the straight segments 15a, 16a prolonging the annular segments 15, 16 respectively are inserted into recesses 17, 18 of ring 9, the annular segments are prevented from rotating around the axes of rods 19, 20 respectively when abutment means 27, 28 are actuated.

An animal is positioned in the plethysmographic chamber by withdrawing the hollow piston 4 from the cylindrical part 2 and moving the annular segments 15, 16 away from one another in order to open the collar to its maximum extent. The animal is then inserted by placing its snout through the openings in the elastomer rings 13, 14. The hollow piston 4 is re-inserted so as to limit the chamber volume to the minimum necessary for the animal's body. The collar opening is then tightened by actuating means 25 and 26. From this moment, the animal can no longer withdraw its head into the chamber extending between piston 4 and rings 13 and 14.

Duct 7 is then connected to a measuring transducer (not shown) and the respiratory tests can begin.

We claim:

1. A plethysmographic measuring chamber for receiving the body of a laboratory animal for measuring respiratory parameters, which chamber has two ends and comprises:
a tubular body having a front end, and a tapered portion at said front end, said tapered portion terminating in a aperture for admitting a flow of gas to the chamber for inhaling by the animal therein; adjacent said aperture, two annular seals spaced apart along a longitudinal chamber axis and provided with openings for admitting the snout of an animal placed in the chamber, said seals defining one end of the chamber; a movable wall defining the other end of the chamber; and adjustable in position to adapt the volume of the chamber to the size of the animal therein; and a retaining collar disposed in the spacing between the said seals, and comprising two mutually opposite members each concave towards said axis of the chamber, mounting means for said concave members such that said members are movable towards and away from one another, and positioning means external to the chamber, adapted to position said concave members at selected radial positions relative to said chamber axis.

2. The plethysmographic chamber of claim 1 further comprising, for each said concave member, a mounting rod extending radially with respect to said chamber axis, extending through a wall of said chamber body and slidable in said wall, said rod being secured substantially centrally to the respective concave member, resilient means biasing each said rod radially inwards towards said chamber axis, an abutment means secured on the outermost end of each said rod external to the chamber, a cam member mounted on and rotatable about each said rod adjacent the abutment means, and for each said cam member a cooperating cam secured to said body such that said cam and cam member cooperatively define two different axial positions of each rod against the resilient bias of the respective resilient means, thereby defining two radial positions of each concave member relative to said chamber axis.

3. The plethysmographic chamber of claim 2 in which each said concave member has, at at least one end thereof, a segment projecting away from the said chamber axis, and guide means provided internally in said wall of said body between said seals and receiving said outwardly projecting segments, for preventing rotation of said concave members about a longitudinal axis of said rods.

4. The plethysmographic chamber of claim 2 or 3 in which the abutment means are screw-threaded to the outer ends of said rods, such that the positions of said abutment means on said rods can be adjusted.

* * * * *